(12) United States Patent
Parab et al.

(10) Patent No.: US 7,087,429 B2
(45) Date of Patent: Aug. 8, 2006

(54) PROCESS FOR PROLIFERATION AND DIFFERENTIATION OF RAT ASCINAR CELLS

(75) Inventors: Pradeep Bhaskar Parab, Pune (IN); Anil Chatterji, Dona Paula (IN)

(73) Assignee: Department of Biotechnology and Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/807,682

(22) Filed: Mar. 24, 2004

(65) Prior Publication Data

US 2004/0180324 A1    Sep. 16, 2004

Related U.S. Application Data

(63) Continuation of application No. 10/112,079, filed on Mar. 29, 2002, now abandoned.

(60) Provisional application No. 60/280,085, filed on Mar. 30, 2001.

(51) Int. Cl.
*C12N 5/00*    (2006.01)

(52) U.S. Cl. ............... 435/325; 424/538; 424/561; 424/581

(58) Field of Classification Search ........ 435/325; 424/538, 561, 581
See application file for complete search history.

*Primary Examiner*—Ralph Gitomer
(74) *Attorney, Agent, or Firm*—Ladas & Parry LLP

(57) ABSTRACT

A process for obtaining a substance with growth promoting activity that includes the step of isolating perivitelline fluid from a fertilized egg of a horseshoe crab. Also, a process for proliferating cells including the steps of isolating perivitelline fluid from a fertilized egg of a horseshoe crab and growing the cells in the presence of the isolated perivitelline fluid.

4 Claims, No Drawings

PROCESS FOR PROLIFERATION AND DIFFERENTIATION OF RAT ASCINAR CELLS

CROSS-RELATED APPLICATIONS

This application is a Continuation of application Ser. No. 10/112,079 filed on Mar. 29, 2002 now abandoned, which claims the benefit of U.S. Provisional Application No. 60/280,085 filed Mar. 30, 2001.

FIELD OF THE INVENTION

This invention relates to the identification and characterization of cell proliferating factor in the perivitelline fluid of the fertilized eggs of the Indian horseshoe crab.

BACKGROUND OF THE INVENTION

The regeneration of pancreatic β-cells has become an important factor for the purpose in curing *Diabetes mellitus*. The concept that β-cell mass is static has changed and now we know that β-cells are dynamic and to certain extent can compensate for the loss of blood glucose and retain their ability to respond to changes in blood glucose by their ability to maintain glucose homeostasis. These studies are based on the experimental animal models. In continuation with the same efforts have been made to search for the factors that lead to direct differentiation of β-cells from precursor cells and those responsible for proliferation of existing β-cells in the residual β-cell mass in the diabetic individual. The aims of these efforts are to find out novel molecules to control and cure diabetes by natural products.

Rat AR42J is derived from a chemically induced pancreatic tumor having exocrine origin and has the feature of pluri-potency of the common precursor cell of the pancreas. It has been reported that amylase secreting AR42J cells convert themselves into insulin secreting cells in the presence of hepatocyte growth factor and or in the presence of betacellulin and activin A. Reference may be made to a publication wherein rat AR42J cells were derived from a chemically induced pancreatic tumor having exocrine origin and have the feature of pluri-potency of the common precursor cell of the pancreas (Mashima H, Ohnishi H, Wakabayashi K. Mine T., Miyagawa J, Hanahusa Ta, Seno M, Yamada H, Kojima I, *Betacellulin and activin A coordinately convert amylase-secreting pancreatic AR42J cells in to insulin-secreting cells, J. Clin Invest* 97:1647–1654, 1996; Mashima H, Yamada S, Tajima T., Seno M, Yamada H, Takeda J and Kojima I. *Genes Expressed During the differentiating of Pancreatic AR42J cells into insulin-secreting cells, Diabetes,* 48, p 304–309, 1999).

OBJECT OF THE INVENTION

The main object of the invention is to identify and isolate insulin producing beta cell differentiating factor from the perivitelline fluid of the fertilized eggs of Horseshoe crab.

It is a further object of the invention to achieve the differentiation of pancreatic AR42J cells into insulin producing cells.

It is another object of the present invention to provide a new process for isolation of new growth promoting activity from the pervitelline fluid collected from the fertilized eggs of the horseshoe crab that facilitates the proliferation of AR42J cells.

It is further object of the invention to achieve the fractionation of potential putative differentiating factor from perivitelline fluid of a Horseshoe crab.

SUMMARY OF THE INVENTION

Accordingly, the present invention provides a process for identification of insulin producing β-cells proliferating factor from the perivitelline fluid of fertilized eggs of horseshoe crab that facilitates the proliferation of AR42J cells from rat origin.

In one embodiment of the invention, the process comprises collecting perivitelline fluid from the fertilized eggs of the Indian horseshoe crab.

In another embodiment of the invention, the perivitelline fluid is collected asceptically, aliquoted and stored at $-20°$ C.

In a further embodiment of the invention, the AR42J cell line (rat ascinar cells) obtained from American Type Culture Collection (ATCC) P.O. Box 1549, Manasses, Va. 20108, USA, was grown in Dulbecco's modified minimum essential medium supplemented with 10% FCS.

In a further embodiment of the invention, the cells were maintained in NUNC six-well dishes (NUNCLON, Denmark).

In another embodiment of the invention, a subculture was done every $4^{th}$ day of seeding of $1\times10^5$ cells and the cultures were incubated at $37°$ C.

In yet another embodiment of the invention, concentration dependent proliferation was observed in presence of pervitelline fluid.

DETAILED DESCRIPTION OF THE INVENTION

In preliminary studies it was observed that perivitelline fluid collected from the fertilized eggs of the horseshoe crab has proliferative and differentiating activity in AR42J cell line of rat pancreas.

The aforesaid process requires absolute precaution for bacterial and fungal contamination at all above processing steps. All apparatus and reagents must therefore, by pyrogen free. The novelty of the present invention is in identification of a new growth promoting activity from the pervitelline fluid collected from the fertilized eggs of the horseshoe crab that facilitates the proliferation of AR42J cells of rat origin.

METHODOLOGY

1. Collection of Pervitelline Fluid from the Fertilized Eggs of the Horseshoe Crab:

Fertilized eggs of the horseshoe crab were collected from the nests located on the sandy beach at Balramgari (Orissa). The fertilized eggs were transferred in filtered seawater and incubated at a constant in artificial incubators. As soon as the eggs became transparent, showing the movement of trilobite larvae, the perivitelline fluid was collected aseptically, aliquoted and stored at $-20°$ C.

2. Cell Culture:

AR42J cell line (rat ascinar cells) obtained from American Type Culture Collection (ATCC) P.O. Box 1549, Manassas, Va. 20108, USA, was grown in Dubecco's modified minimum essential medium supplemented with 10% FCS. The cells were maintained in NUNC six-well dishes (NUNCLON, Denmark). Subculture was done every fourth day of seeding of $1\times10^5$ cells and the cultures were incubated at $37°$ C. in 5% $CO_2$ atmosphere. AR42J cells were grown in presence of perivitelline fluid and 3H-thymidine for 72 hours at 37° C. Concentration dependent proliferation was observed (Table 1). Studies were being carried out to see mRNA expression of insulin in AR42J in presence of perivitelline fluid.

EXAMPLE

Fertilized eggs of the horseshoe crab were collected from the nests located on the sandy beach at Balramgari (Orissa). The fertilized eggs were transferred in filtered seawater and incubated at a constant in artificial incubators. As soon as the eggs became transparent, showing the movement of trilobite larvae, the perivitelline fluid was collected asceptically, aliquoted and stored at −20° C.

AR42J cell line (rat ascinar cells) obtained from American Type Culture Collection was grown in Dulbecco's modified minimum essential medium supplemented with 10% FCS. These cells were maintained in NUNC six-well dishes (NUNCLON, Denmark). Sub culture was done every $4^{th}$ day of seeding of $1 \times 10^5$ cells and the cultures were incubated at 37° C. in 5% [$Co_2$]$CO_2$ atmosphere. AR42J cells were grown in presence of perivitelline fluid and proliferative activity of perivitelline fluid was observed which was found to be concentration dependent (Table 1). Pervitelline fluid showed significant proliferation of AR42J cell lines which is reported for the first time.

TABLE 1

Percent increase in cell population in presence of perivitelline fluid

| Perivitelline (µg/ml) | 3H-counts/min | % increase |
|---|---|---|
| 0.0 | 1678 | — |
| 1.0 | 2377 | 041 |
| 2.5 | 3115 | 085 |
| 5.0 | 8662 | 416 |
| 10.0 | 13083 | 680 |

Advantage: Identification of the new growth factor will be useful for cell proliferation.

We claim:
1. A process for proliferating or differentiating cells, comprising the steps of:
  i) providing rat acinar cells from the AR42J cell line; and
  ii) growing the cells in the presence of perivitelline fluid from a fertilized egg of a horseshoe crab to cause proliferating or differentiating of the cells.
2. The process as claimed in claim 1, wherein the cells are grown in Dulbecco's modified minimum essential medium supplemented with 10% fetal calf serum (FCS).
3. The process as claimed in claim 1, further comprising measuring an increase in population of the cells.
4. The process as claimed in claim 1, wherein the horseshoe crab is an Indian horseshoe crab.

* * * * *